United States Patent
Matonick et al.

(10) Patent No.: US 10,130,368 B2
(45) Date of Patent: Nov. 20, 2018

(54) EXPANDABLE COMPRESSION RINGS FOR IMPROVED ANASTOMOTIC JOINING OF TISSUES

(71) Applicant: Ethicon, Inc., Somerville, NJ (US)

(72) Inventors: John Matonick, Warren, NJ (US); Robert J. Tannhauser, Bridgewater, NJ (US); Leo B. Kriksunov, Ithaca, NY (US)

(73) Assignee: Ethicon, Inc., Somerville, NJ (US)

(*) Notice: Subject to any disclaimer, the term of this patent is extended or adjusted under 35 U.S.C. 154(b) by 393 days.

(21) Appl. No.: 15/088,499

(22) Filed: Apr. 1, 2016

(65) Prior Publication Data

US 2017/0281181 A1    Oct. 5, 2017

(51) Int. Cl.
*A61B 17/04* (2006.01)
*A61B 17/10* (2006.01)
(Continued)

(52) U.S. Cl.
CPC .... *A61B 17/1114* (2013.01); *A61B 17/07292* (2013.01); *A61B 17/1155* (2013.01);
(Continued)

(58) Field of Classification Search
CPC ............................................... A61B 17/07292
(Continued)

(56) References Cited

U.S. PATENT DOCUMENTS 4,612,337 A * 9/1986 Fox, Jr. .................... A61L 27/54
424/423
5,250,058 A * 10/1993 Miller .................... A61B 17/11
24/615
(Continued)

FOREIGN PATENT DOCUMENTS

DE    19732234    1/1999
EP     2139406    11/2008
(Continued)

OTHER PUBLICATIONS

International Search Report re: PCT/US2017/024466 dated Jun. 29, 2017.
(Continued)

*Primary Examiner* — Andrew M Tecco
*Assistant Examiner* — Eyamindae Jallow
(74) *Attorney, Agent, or Firm* — David R. Crichton; Leo B. Kriksunov (57) ABSTRACT

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, prevent tissue infection, and to prevent leakage. The present invention further relates to an expandable compression device for application to anastomotically joined tubular tissues, comprising: an upper ring-shaped or disk-shaped flange at a distal end of said device connected to a lower ring-shaped inflatable flange at a proximal end of said device via a hollow cylindrical tubular body, with an opening forming an axial passage through said upper flange, lower flange, and tubular body.

9 Claims, 11 Drawing Sheets

(51) Int. Cl.
*A61B 17/11* (2006.01)
*A61B 17/072* (2006.01)
*A61B 17/115* (2006.01)
*A61B 17/00* (2006.01)

(52) U.S. Cl.
CPC ............ *A61B 2017/00004* (2013.01); *A61B 2017/00557* (2013.01); *A61B 2017/00889* (2013.01); *A61B 2017/07257* (2013.01); *A61B 2017/1103* (2013.01); *A61B 2017/1132* (2013.01)

(58) Field of Classification Search
USPC ..... 227/19, 175.1, 176.1; 606/153, 154, 219
See application file for complete search history.

(56) References Cited

U.S. PATENT DOCUMENTS

| | | | |
|---|---|---|---|
| 5,271,544 A | | 12/1993 | Fox et al. |
| 5,904,703 A | * | 5/1999 | Gilson ............... A61B 17/0057 606/213 |
| 7,527,185 B2 | | 5/2009 | Harari et al. |
| 7,645,288 B2 | | 1/2010 | McKenna et al. |
| 2003/0183671 A1 | | 10/2003 | Mooradian et al. |
| 2005/0059997 A1 | * | 3/2005 | Bauman ............... A61B 17/072 606/219 |
| 2006/0085034 A1 | * | 4/2006 | Bettuchi ............... A61B 17/115 606/219 |
| 2006/0135992 A1 | * | 6/2006 | Bettuchi ............... A61B 17/072 606/219 |
| 2006/0271104 A1 | * | 11/2006 | Viola ............... A61B 17/00491 606/214 |
| 2007/0060923 A1 | * | 3/2007 | Dreyfuss ............. A61B 17/0642 606/75 |
| 2009/0138030 A1 | | 5/2009 | Gronberg |
| 2010/0036399 A1 | * | 2/2010 | Viola ..................... A61B 17/11 606/153 |
| 2010/0147923 A1 | * | 6/2010 | D'Agostino ......... A61B 17/072 227/179.1 |
| 2011/0098724 A1 | * | 4/2011 | Cichocki ............... A61L 17/005 606/139 |
| 2014/0358167 A1 | * | 12/2014 | Armstrong ....... A61B 17/07292 606/153 |

FOREIGN PATENT DOCUMENTS

| | | |
|---|---|---|
| WO | WO 2004/086984 | 10/2004 |
| WO | WO 2008135083 | 11/2008 |
| WO | WO 2012/007044 | 1/2012 |

OTHER PUBLICATIONS

Written Opinion re: PCT/US2017/024466 dated Jun. 29, 2017.
K. Jonsson, H. Jiborn, B. Zederfedt, "Breaking strength of small intestinal anastomoses", *The American Journal of Surgery*, v. 145, pp. 800-803, 1983.
Y.-H. Ho, M.A.T. Ashour, "Techniques for colorectal anastomosis", *World Journal of Gastroenterology*, 16(13), pp. 1610-1621, 2010.

* cited by examiner

EXPANDABLE COMPRESSION RINGS FOR IMPROVED ANASTOMOTIC JOINING OF TISSUES

FIELD OF THE INVENTION

The present invention relates to surgical instruments and methods for enhancing properties of tissue repaired or joined by surgical staples and, more particularly to surgical instruments and methods designed to reinforce and isolate the repaired or adjoined tissue at a target surgical site.

BACKGROUND OF THE INVENTION

Throughout the years the medical field has utilized various techniques in an effort to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples are used to replace suturing when joining or anastomosing various body structures, such as, for example, the bowel. The surgical stapling devices employed to apply staples are generally designed to simultaneously cut and seal an extended segment of tissue in a patient.

Linear or annular/circular surgical stapling devices are employed by surgeons to sequentially or simultaneously apply one or more rows of surgical fasteners, e.g., staples, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular or circular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis in a separate step.

U.S. Pat. No. 7,645,288 "Anastomotic ring applier with inflatable members", assigned to ETHICON ENDO SURGERY INC. describes a surgical instrument comprises a handle connected to a shaft and a pair of inflatable members. The shaft includes conduits for communicating a pressurized medium to the inflatable members and an insufflation tube. The handle includes a port for communicating a pressurized medium to the conduits and a port for communicating a pressurized medium to the insufflation tube. After an anastomotic ring has been deployed, the shaft may be positioned such that an inflatable member is positioned within each of the lumens joined by the anastomosis, such that an inflatable member is located on each side of the anastomosis. The inflatable members may be inflated to provide a seal in each of the lumens. With each of the lumens sealed by the inflatable members, the anastomosis site may be insufflated through the insufflation tube to leak or pressure test the anastomosis.

According to the cited patent, a surgical instrument operable to test an anastomosis, wherein the anastomosis is located at an anastomosis site in a patient, the instrument comprising: (a) a handle; (b) a tip; (c) a tip actuator, wherein the tip actuator is configured to move the tip from a retracted position to an extended position; (d) a shaft connected to the handle, the shaft comprising: (i) an outer surface, (ii) a proximal end, wherein the handle is located at the proximal end of the shaft, (iii) a distal end, wherein the distal end of the shaft comprises two or more inflatable members adjacent the outer surface, wherein the two or more inflatable members are spaced to permit at least one inflatable member of the two or more inflatable members to be positioned on a first side of the anastomosis and another at least one inflatable member of the two or more inflatable members to be positioned on a second side of the anastomosis, wherein the at least one inflatable member is configured to provide a seal of at least one of the one or more lumens, wherein the seal is adjacent the anastomosis, wherein the seal is provided upon inflation of the at least one inflatable member, (iv) one or more conduits configured to communicate a pressurized medium to at least one of the two or more inflatable members, and (v) a tubular sheath, wherein the tubular sheath is moveable from a first position to a second position; (e) a ring deployment mechanism located at the distal end of the shaft adjacent the two or more inflatable members, wherein the ring deployment mechanism is operable to deploy an anastomotic ring at the anastomosis site, wherein the ring deployment mechanism defines a longitudinal axis, wherein the ring deployment mechanism comprises: (i) a proximal ring situated about said longitudinal axis, (ii) a first plurality of fingers, wherein each finger of the first plurality of fingers comprises a proximal segment and a distal segment, wherein the proximal segment of each finger of the first plurality of fingers is hingedly connected to the corresponding distal segment of the same finger of the first plurality of fingers at a corresponding finger joint, wherein the proximal segment of each finger of the first plurality of fingers is further hingedly connected to said proximal ring, wherein the first plurality of fingers are configured to engage the anastomotic ring at regions adjacent to the finger joints of the first plurality of fingers, (iii) a distal ring situated about said longitudinal axis, (iv) a second plurality of fingers, wherein each finger of the second plurality of fingers comprises a proximal segment and a distal segment, wherein the proximal segment of each finger of the second plurality of fingers is hingedly connected to the corresponding distal segment of the same finger of the second plurality of fingers at a corresponding finger joint, wherein the distal segment of each finger of the second plurality of fingers is further hingedly connected to said distal ring, wherein the second plurality of fingers are configured to engage the anastomotic ring at regions adjacent to the finger joints of the second plurality of fingers, and (v) a middle ring positioned in between said proximal ring and said distal ring, wherein the distal segment of each finger of the first plurality of fingers is further hingedly connected to the middle ring, wherein the proximal segment of each finger of the second plurality of fingers is further hingedly connected to the middle ring, wherein the middle ring longitudinally separates the distal segments of the first plurality of fingers from the proximal segments of the second plurality of fingers; (f) one or more actuators operable to actuate the ring deployment mechanism, wherein the one or more actuators is configured to move along the handle or the shaft; and (g) a tip tube positioned within the shaft, wherein the tip tube has a proximal end and a distal end, wherein the proximal end of the tip tube is coupled with the tip actuator, wherein the distal end of the tip tube is coupled with the tip, wherein the tip actuator is operable to move the tip from a retracted position relative to the tubular sheath to an extended position relative to the tubular sheath via the tip tube; wherein the tip is configured to cover a distal portion of the ring deployment mechanism when the tip is in the retracted position; wherein the tip is configured to uncover the distal portion of the ring deployment mechanism when the tip is in the extended position; wherein the tubular sheath is configured to cover a proximal portion of the ring deployment mechanism when the tubular sheath is in the first position; wherein the tubular sheath is configured to uncover the proximal portion of the ring deployment mechanism when the tubular sheath is in the second position.

As stated in the cited reference, the inflatable members may be inflated to provide a seal in each of the lumens, with each of the lumens sealed by the inflatable members, the anastomosis site may be insufflated through the insufflation tube to leak or pressure test the anastomosis.

European Patent Application publication No. EP2139406A1 or WO2008135083 "AN ANASTOMOTIC APPLIER AND METHOD FOR PERFORMING ENDOLUMENAL AND/OR TRANSLUMINAL ANASTOMOSIS", assigned to ETHICON ENDO SURGERY INC., discloses an anastomotic ring applier system for deploying a first compression ring and a second compression ring, comprising an anastomotic applier including: a second ring carrier adapted to hold the second compression ring; a ring approximation device with a first portion connectable to an external first ring carrier device which supports said first compression ring and a second portion connected to said second ring carrier device, wherein the first portion forms a first thread and the second portion forms a second thread meshing the first thread; a rotary device acting on at least one of said first and second portions and configured to rotate the first and second portions to one another so that they translate to one another to approximate and interconnect the compression rings. The reference further discloses that the anastomotic ring applier system further includes a coupling device which comprises: a coupling portion connected to the first ring carrier and having an inflatable anchoring head, a catching portion connected to the ring approximation device and defining a receiving space for receiving at least part of the anchoring head and an access aperture through which the anchoring head is insertable from outside the catching portion into the receiving space, an activating device connected to the anchoring head and configured to deform the anchoring head such that it can take on an expanded configuration and a retracted configuration, wherein the access aperture is configured to allow insertion and withdrawal of the anchoring head when it is retracted and to lock the at least partially inserted anchoring head to the catching portion when it is expanded such as to firmly couple the approximation device to the first ring carrier device.

Various compression anastomotic ring systems have been pursued as a replacement to the staple-based anastomotic closure. For example, LARA™ compression anastomotic ring system developed by novoGI™ utilizes nitinol-based compression ring specifically targeting low anterior resection (LAR) procedures.

U.S. Pat. No. 7,527,185 "Compression anastomosis ring assembly and applicator for use therewith" assigned to Niti Surgical Solutions Ltd., discloses a compression anastomosis ring (CAR) assembly which comprises: a first portion which comprises: an anvil ring; and a second portion which comprises: a bottom ring positioned substantially parallel to and spaced apart from said anvil ring, said anvil ring and said bottom ring being adapted to be brought together in the presence of a closure force applied there across: at least one ring element, where one of said at least one ring elements is a needle ring positioned on a side of said bottom ring distal from said anvil ring, said needle ring having a plurality of needles extending generally transversely therefrom toward said first portion; and at least one spring element which provides a restorative force formed at least partially of a shape-memory alloy, said spring element positioned on one of said at least one ring elements and being in compressive force transmissive contact with said bottom ring, and wherein when said compression anastomosis ring (CAR) assembly is positioned so as to hold between said anvil ring and said bottom ring tissue portions to be compressed and joined by anastomosis, said needle ring is operative, in response to the closure force to drive said plurality of needles through the tissue portions to be compressed and to anchor said plurality of needles in said anvil ring, and wherein when said anvil ring and said bottom ring are brought together in the presence of the closure force holding the tissue portions therebetween, and when said anvil ring is anchored by said plurality of needles, the restorative force provided by said at least one spring element is operative on said bottom ring to compress said tissue portions thereby effecting anastomosis.

U.S. Pat. No. 5,250,058 "Absorbable anastomosic fastener means" assigned to ETHICON INC., discloses a mechanism which is capable of anastomosis of two lumens by an absorbable fastener. The fastener is made from two washer-like plates. One such plate has holes to receive latching prongs protruding from the other plate. Fastening is done through a single linear motion that causes the prongs to pierce the tissue, latches the prongs into a receiver and causes a knife blade to cut through excess fastener material and tissue. The ease of removal, by pulling the mechanism through the formed anastomosis, is greatly enhanced. The system can be used such that the plates can be placed in any configuration to properly anastomose tissue. The patent discloses a compression anastomosis device comprising: a piercing ring containing a plurality of piercing flanges; a receiving ring containing a plurality of receiving slots corresponding to said flanges; and spring means placed between said piercing and receiving rings to exert a spring force on one of said piercing and receiving rings.

Post-operative leakage of the stapled tissue seals, including anastomotic seals has been shown to lead to morbidity and mortality. A number of technologies are related to direct application of material to the serosal layer after stapling by either dripping or spraying. The problems associated with these techniques are that access is very difficult and visual assessment as to whether or not the material was applied to the right spot and completely around the anastomosis. The material is also applied on top of the serosal layer when the target site is actually subserosal along the staple line. Applying a therapeutic agent to the serosal layer of the colon requires the material to migrate through the serosa and to the staple region, then provide a biological affect, and overcome the problems associated with a leak formation, all within 24-48 hours, assuming the material was applied to the correct spot intra operatively. One of the most challenging steps in the application of a topical adjunctive therapy to a colorectal anastomosis is to provide the material to the site because of the extreme limitation in access to the site. Some colorectal anastomoses are performed relatively "low" in a patient (i.e. lower anterior resection) and the actual staple line is deep within the pelvic canal, which makes a topical application of material around the circumference very difficult.

The known compression anastomotic rings lack the reliability of stapled anastomosis. The staple based anastomotic joining is a widely accepted practice but there is a need in improving the technology to prevent post-operative leakage of the stapled tissue seals to improve the viability of the tissue joined by staples.

SUMMARY OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, prevent tissue infection, and to prevent leakage.

The present invention, in one aspect, relates to a circular surgical stapler for anastomotic joining of tissue having a stapling head connected to an opposing anvil, with stapling head containing a plurality of deployable staples in concentric arrays, and to a compression device deployable from the stapler onto the stapled anastomotic joint.

The present invention, in another aspect, relates to a circular stapling instrument comprising: an anvil, a stapling head assembly; a moveable shaft connecting the anvil and staple head assembly; a longitudinal shaft from which the moveable shaft extends; a compression device removeably affixed to the anvil and having an upper ring-shaped or disk-shaped flange at a distal end of said device connected to a lower ring-shaped expandable flange at a proximal end of said device via a hollow cylindrical tubular body and an opening forming an axial passage through said upper flange, lower flange, and tubular body.

The present invention, in yet another aspect, relates to a method of establishing an anastomotic joint between tubular tissue lumens with an anastomotic stapler, the stapler having a stapling head connectable to an opposing anvil and the stapling head containing a plurality of deployable staples, the method comprising the steps of: axially positioning on the anvil a compression device having an upper ring-shaped or disk-shaped flange at a distal end of said device connected to a lower ring-shaped expandable flange at a proximal end of said device via a hollow cylindrical tubular body and an opening forming an axial passage through said upper flange, lower flange, and tubular body; axially inserting the anvil into a first tubular tissue; axially inserting the anastomotic stapler into a second tubular tissue; connecting the anvil to the stapling head via an anvil shaft; approximating the anvil and the stapling head and compressing said first and second tubular tissues between the stapling head and the anvil; firing the anastomotic stapler and establishing the anastomotic joint between said first and second tubular tissues; partially withdrawing the anastomotic stapler thus positioning said compression device with said upper flange above stapled areas of said first and second tubular tissues and said lower flange below the stapled areas of said first and second tubular tissues; expanding said upper flange; expanding said lower flange, thus compressing the stapled areas of said first and second tubular tissues between the upper flange and the lower flange; removing the anastomotic stapler from the tubular tissues; separating the anastomotic stapler from the compression device; and leaving the compression device within said first and second tubular tissues with the upper flange above the stapled areas and the lower flange below the stapled areas.

DETAILED DESCRIPTION OF THE INVENTION

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-op leakage of the anastomosis has been shown to lead to morbidity and mortality.

Typical surgical stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component.

Figure 1:
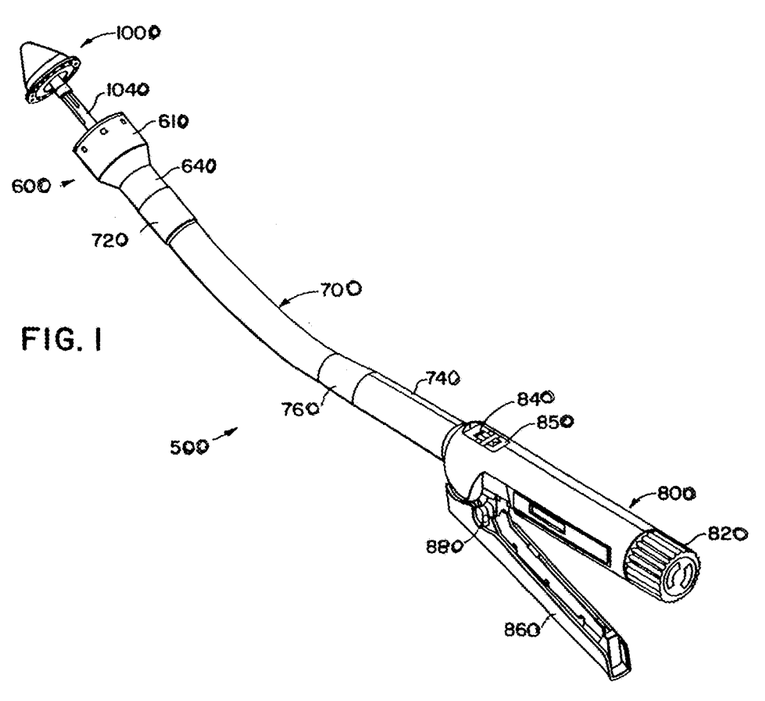
FIG. 1 shows a perspective view of a typical circular surgical stapling instrument

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 500 includes a distal stapling head assembly 600 connected by a longitudinally curved support shaft assembly 700 to a proximal actuator handle assembly 800. The stapling instrument includes an anvil assembly or anvil 1000 which is slidable longitudinally relative to the stapling head assembly 600 and mounted on an axially extending moveable shaft 1040. An optional rotatable adjusting knob 820 is provided at the proximal end of the actuator handle assembly 800 for adjusting the spacing between the stapling head assembly 600 and the anvil assembly 1000. Other approximating means to compress adjacent sections of tissue are known to skilled artisans and can be used. An optional movable indicator 840 is visible through an optional window 850 on top of the handle assembly 800 to indicate the staple height and/or gap between the stapling head assembly 600 and anvil 1000 selected by rotation of the adjusting knob 820. The indicator 840 is movable indicating that the anvil gap is within a desired operating range of the stapling instrument 500. The position of the indicator 840 also indicates whether the selected staple height is large or small.

A staple actuating lever 860 is pivotally mounted on the actuator handle assembly 800 for driving the surgical staples from the stapling head assembly 600 when the anvil assembly 1000 is closed to provide the desired staple height. A pivotal latching member 880 is mounted on the handle assembly 800 for locking the staple actuating lever 860 against movement to preclude actuation of the stapling head assembly 600 when the anvil gap is outside of a predetermined range. The stapling head assembly 600 includes a tubular casing 610 as well as a hollow tubular connector 640 at the proximal end of the casing 610 which receives the distal end of the support shaft 700. A ferrule or sleeve 720 overlaps the joint between the tubular connector 640 and the distal end of the support shaft 700. The proximal end of the support shaft 700 is received by a tubular extension 740 at the distal end of the actuator handle assembly 800. A ferrule or sleeve 760 overlaps the joint between the proximal end of the support shaft 700 and the distal end of the tubular extension 740. The movable indicator 840 is visible through a window 850 on top of the handle assembly 800 to indicate the staple height selected by rotation of the adjusting knob 820.

Other versions and modifications of the circular surgical stapler are known to a skilled artisan. There are typically at least two and frequently more concentric stapling lines or concentric circular rows of staples-containing slots surrounding shaft 1040, with staples in each row typically staggered or offset relative to the staples in the adjacent row, to improve the sealing and prevent leakage along the stapling line.

Clinical evidence shows the formation of a full wall intestinal defect at or near the anastomotic site may occur as soon as 1-2 days post-op, with typical time period when the clinical symptoms of leaks occur being from 1 to 5 days post-op. See, for example, K. Jonsson, H. Jiborn, B. Zederfeldt, "Breaking strength of small intestinal anastomoses", The American Journal of Surgery, v. 145, pp. 800-803, 1983; Y.-H. Ho, M. A. T. Ashour, "Techniques for colorectal anastomosis", World Journal of Gastroenterology, 16(13), pp. 1610-1621, 2010.

According to the present invention, after the staples from a circular anastomotic stapler are deployed and an anastomotic joint is established connecting two parts of a tissue lumen, the circular anastomotic stapler is withdrawn and an inflatable barbell-shaped hollow compression device is installed over the stapled area within the tissue lumen, providing additional reinforcement and particularly isolating the just stapled and just resected areas from contaminations and potential infection. Optionally, a medicant is released from the compression device, such medicant being an antibacterial or anti-infective agent.

Figure 2:
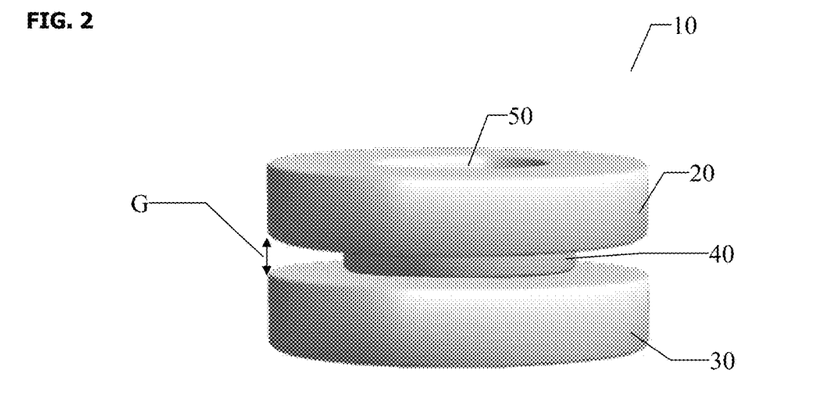
FIG. 2 shows a perspective view of an embodiment of the compression device of the present invention
Figure 3:
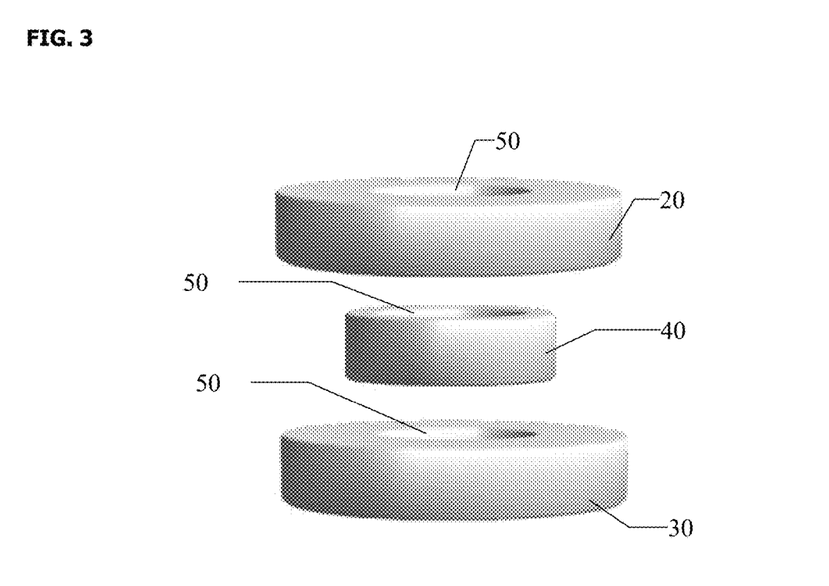
FIG. 3 shows an exploded view of an embodiment of the compression device of the present invention
Figure 4:
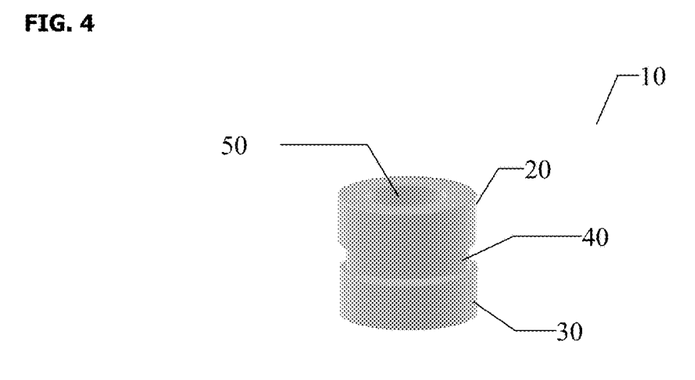
FIG. 4 shows a perspective view of an embodiment of the compression device of the present invention

Referring now to FIG. 2, a schematic perspective view of generally barbell-shaped hollow compression device 10 is shown, with device 10 comprising an upper ring-shaped or toroid-shaped expandable flange 20, such as in one embodiment, inflatable flange 20 connected to a lower ring-shaped or toroid-shaped expandable flange 30, such as in one embodiment, inflatable flange 30 via a hollow cylindrically shaped tubular body 40, with an opening 50 forming an axial passage through all three interconnected components of device 10, i.e. through upper flange 20, tubular body 40, and lower flange 30. FIG. 3 shows an exploded view of device 10 with upper flange 20, tubular body 40, and lower flange 30 shown separately but axially aligned with opening 50 visible in all three components. FIG. 2 shows upper flange 20 and lower flange 30 in the inflated configuration, filled with a fluid such as water, saline, air, nitrogen, or the like. FIG. 4 shows device 10 with upper flange 20 and lower flange 30 in a deflated configuration.

Figure 5:
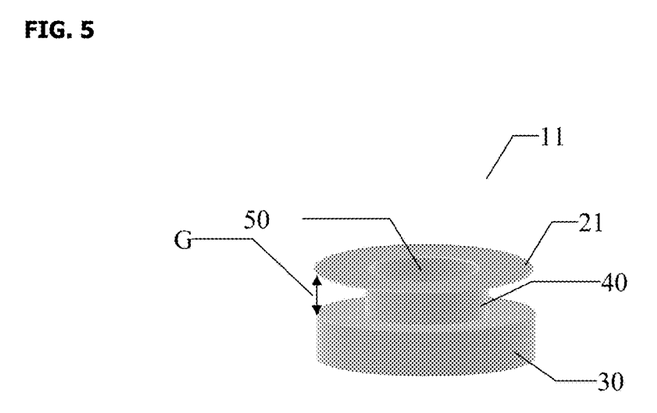
FIG. 5 shows a perspective view of an embodiment of the compression device of the present invention
Figure 6:
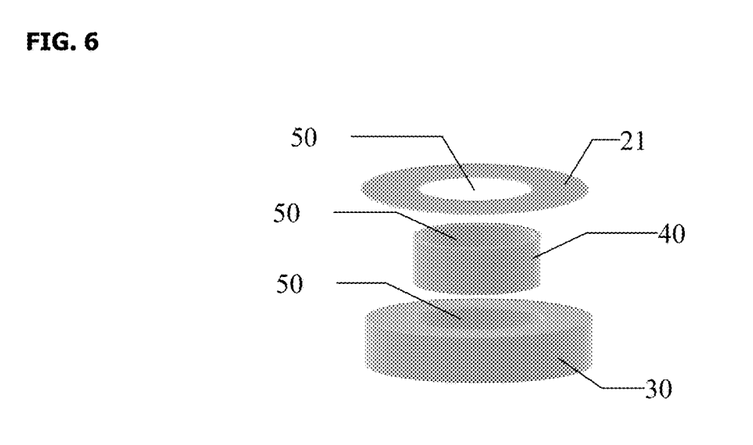
FIG. 6 shows an exploded view of an embodiment of the compression device of the present invention
Figure 7:
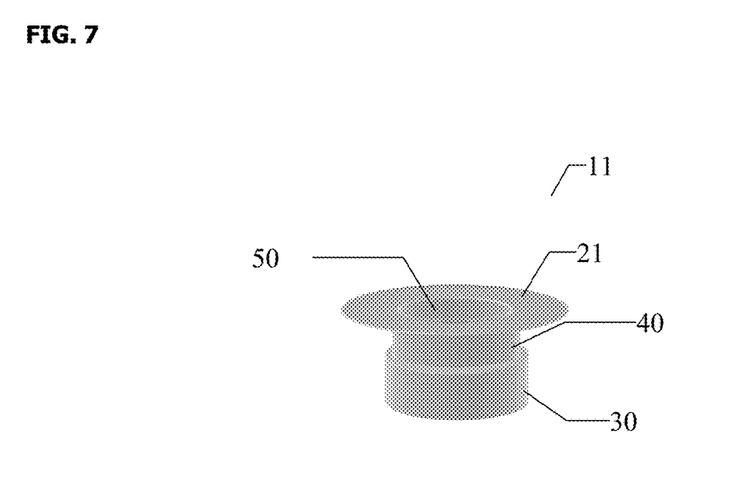
FIG. 7 shows a perspective view of an embodiment of the compression device of the present invention

Referring now to FIG. 5, a schematic perspective view of an alternative embodiment of compression device of the present invention is shown, with generally barbell-shaped hollow compression device 11 comprising an upper disk-shaped non-inflatable flange 21 connected to a lower ring-shaped or toroid-shaped inflatable flange 30 via a hollow cylindrically shaped tubular body 40, with an opening 50 forming an axial passage through all three interconnected components of device 10, i.e. through upper flange 21, tubular body 40, and lower flange 30. FIG. 6 shows an exploded view of device 11 with upper flange 21, tubular body 40, and lower flange 30 shown separately but axially aligned with opening 50 visible in all three components. FIG. 5 shows lower flange 30 in the inflated configuration, filled with a fluid such as water, saline, air, nitrogen, or the like. FIG. 7 shows device 11 with lower flange 30 in a deflated configuration.

The ring-shaped or disk-shaped flanges are understood to have any shapes suitable for functioning in a manner described in this invention.

Gap G between upper flange 20 or 21 and lower flange 30 is shown in FIGS. 2 and 5, when upper flange 20 and lower flange 30 are inflated.

Figure 8:
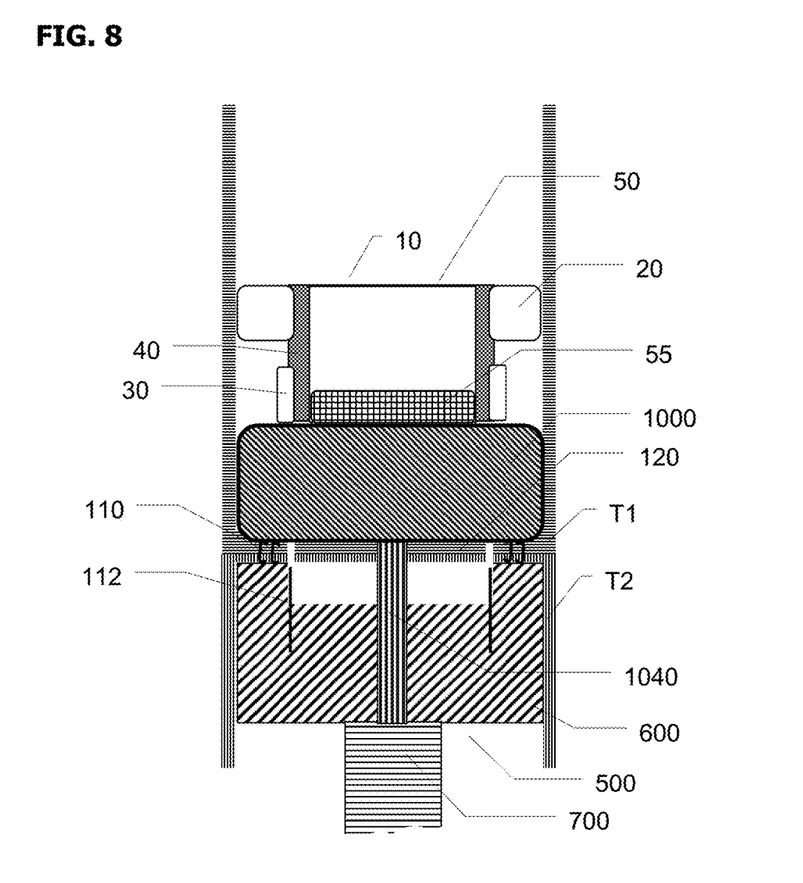
FIGS. 8, 9 and 10 show a schematic side cross-sectional view of a portion of a circular stapler and of the compression device of the present invention in operation.
Figure 9:
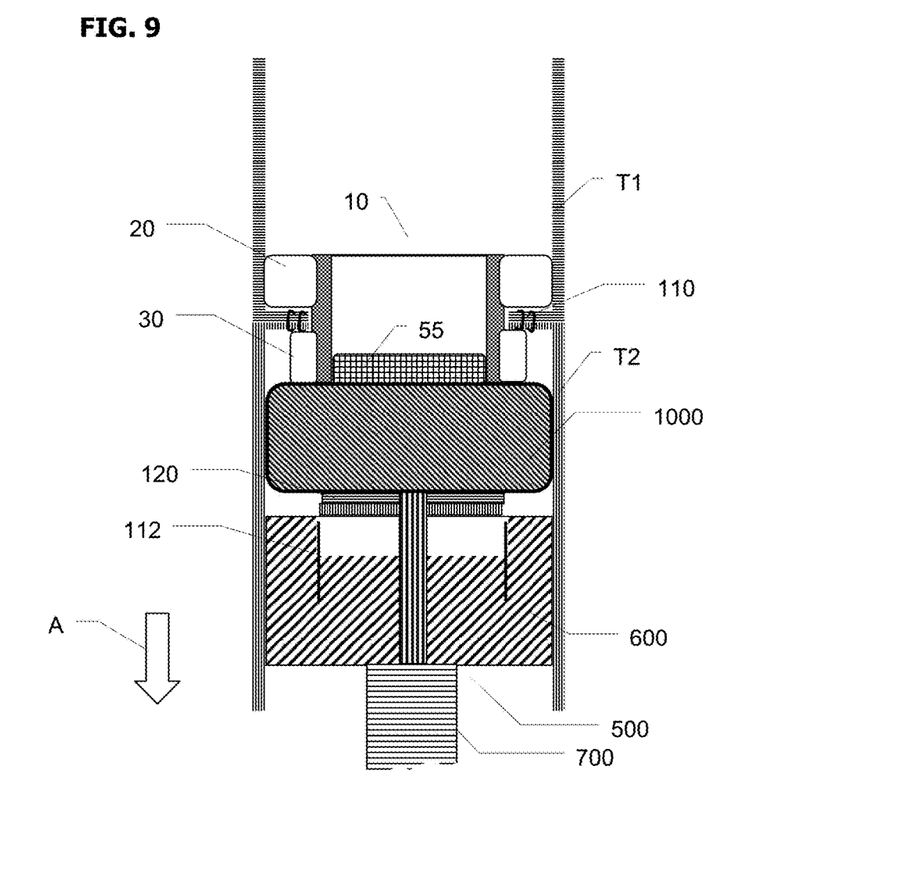
Figure 10:
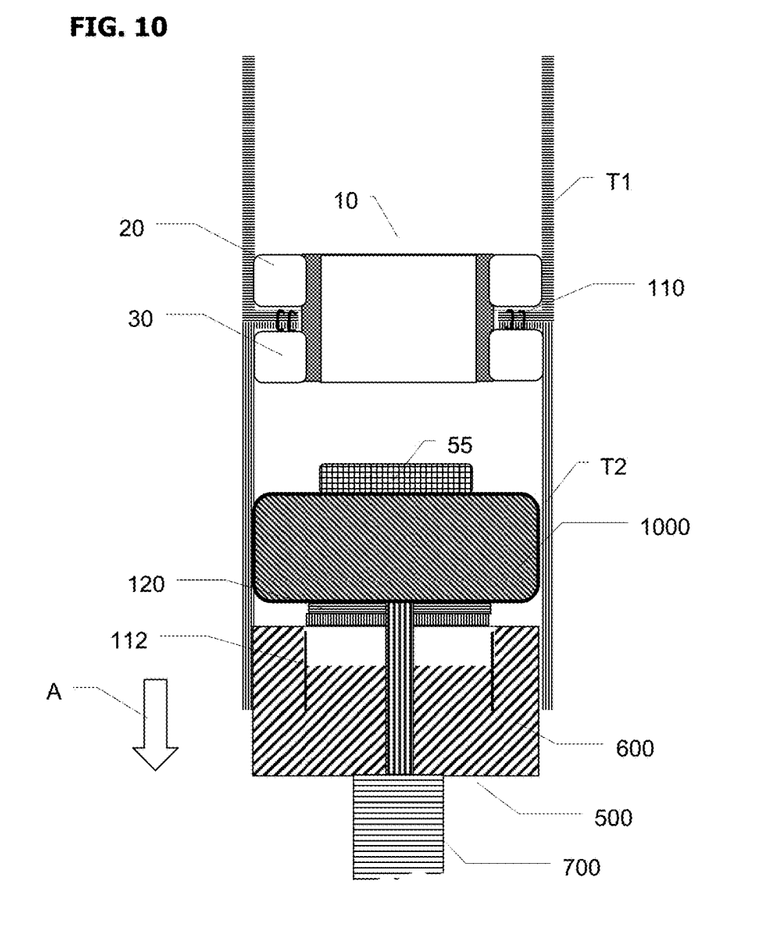

Referring now to FIG. 8, a schematic cross-sectional partial view of a portion of circular stapler 500 performing anastomotic joining of tubular tissues T1 and T2 is presented. Anvil 1000 is shown disposed within tubular tissue T1 and connected to stapling head 600 via moveable shaft 1040. Anvil 1000 can be of any suitable shape or form, such as of generally widely used conical form as shown in FIG. 1, or of generally flat cylinder or disk form, as schematically shown in FIGS. 8-10 or any other form such as a trapezoidal, toroidal or the like. Stapling head assembly 600 is shown disposed within tubular tissue T2 and supported on support shaft assembly 700. For simplification, the mechanism of staples 110 deployment and mechanism of deploying tissue cutting concentric knife 112 are not shown. FIG. 8 shows anvil 1000 and stapling head 600 approximated, compressing tissue T1 and T2 between them, with staples 110 fired thus establishing a stapled joint between tissues T1 and T2 with staples 110 concentrically arranged in one or more concentric rows around tissue donut or cut-out 120.

Compression device 10 is shown disposed within tubular tissue T1 and removably attached onto anvil 1000 via means of attachment, such as via snug fit of pin 55 into opening 50 within tubular body 40. Pin 55 is positioned attached to or machined on top of anvil 1000. Upper inflatable flange 20 is shown at least partially expanded or inflated, whereby lower inflatable flange 30 is in unexpanded, deflated configuration.

As shown in FIG. 9, after deploying staples and cutting out tissue cutout 120, circular stapler 500 is being withdrawn in the direction of arrow A, with anvil 1000 moving past staples 110, pulling device 10 lower inflatable flange 30 also past staples 110. Upper inflatable flange 20 is at least partially or preferably fully expanded or inflated prior to circular stapler withdrawal and thus upper inflatable flange is not brought past staples 110, positioning device 10 with upper flange 20 above staples 110 and within tubular tissue T1 and lower flange 30 below staples 110 and within tubular tissue T2.

As shown in FIG. 10, once device 10 is positioned with upper flange 20 above staples 110 and lower flange 30 below staples 110, upper flange is optionally additionally inflated if needed to achieve full inflation. Lower flange 30 is also fully inflated thus immobilizing device 10 around staples 110 compressing staples 110 lines from above and below and isolating areas of tubular tissues T1 and T2 that were cut and stapled tissue. Circular stapler 500 is then fully withdrawn severing anvil 1000 connection to device 10 via pin 55. Device 10 is positioned with upper flange 20 above staples 110 and within tubular tissue T1 and lower flange 30 below staples 110 and within tubular tissue T2.

Figure 11:
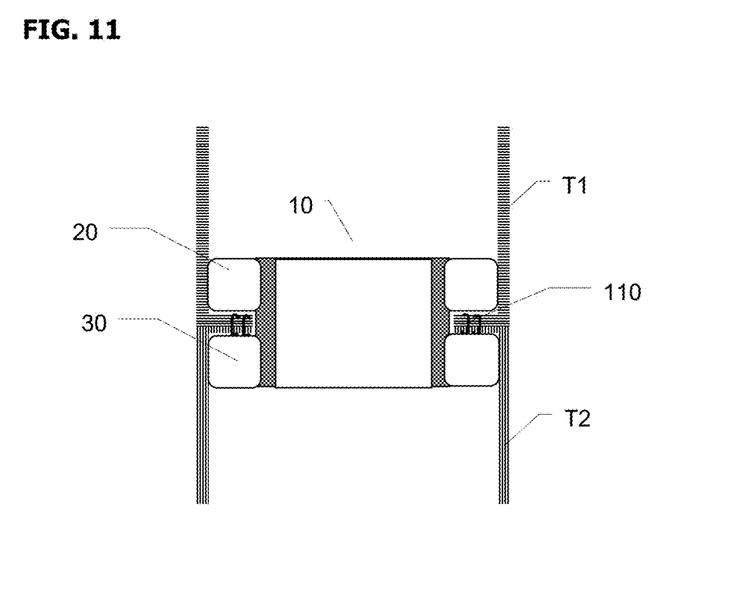
FIGS. 11, 12, 13, 14 and 15 show a schematic side cross-sectional view of an embodiment of the compression device of the present invention

As shown in FIG. 11, after removal of circular stapler 500, device 10 remains within tubular tissues T1 and T2 which are joined by staples 110, with device 10 immobilized around staples 110 and compressing staple lines from above and below and isolating areas of cut and stapled tissue.

Figure 12:
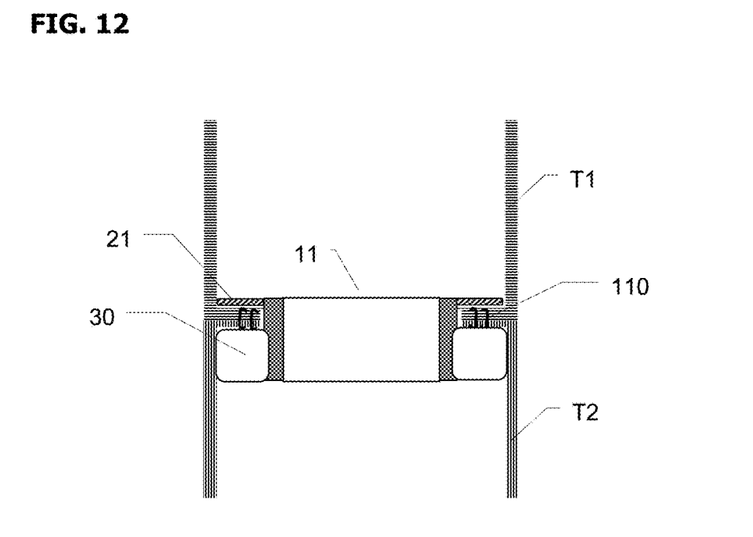

As shown in FIG. 12, compression device 11 which is an alternative embodiment of compression device 10 of the present invention, is installed in a similar fashion, with the upper disk-shaped non-inflatable flange 21 positioned within tissue T1 above staples 110 and lower flange 30 positioned in fully inflated state below staples 110 and within tubular tissue T2.

Figure 13:
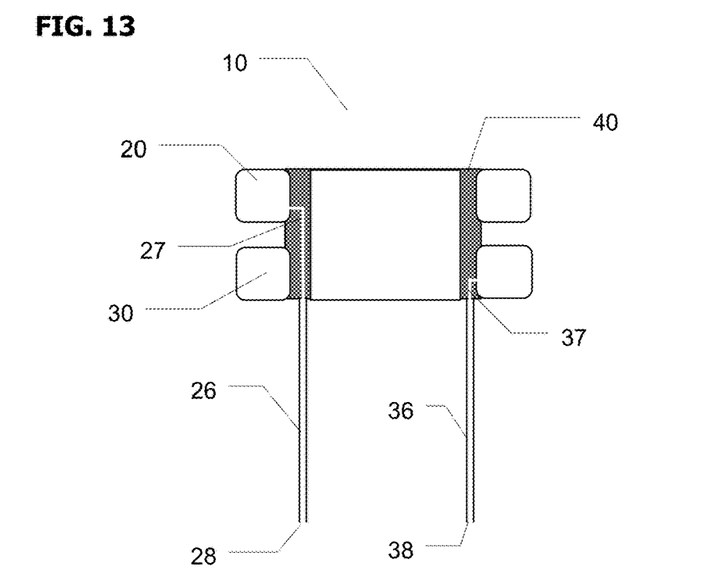
Figure 14:
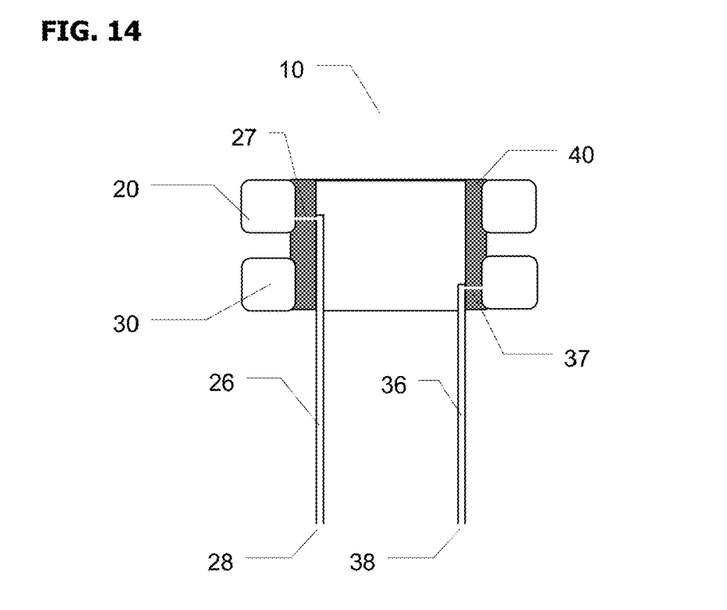

Referring now to FIGS. 13 and 14, embodiments for the inflation means for inflating upper flange 20 and lower flange 30 are shown. Flexible cannula 26 is shown connected to channel 27 in tubular body 40, thus providing fluid communication from cannula 26 inlet 28 to upper flange 20.

Flexible cannula 36 is shown connected to channel 37 in tubular body 40, thus providing fluid communication from cannula 36 inlet 38 to lower flange 30. Inflating is performed by connecting a source of pressurized fluid, such as a syringe containing saline or air, to cannulas 26, 36 inlets 28, 38 and delivering fluid into upper flange 20 and lower flange 30. An optional one way valve (not shown) can be provided in cannulas 26, 36 or in channels 27, 37, or within upper flange 20 and lower flange 30, to prevent deflation. A single cannula (not shown) such as cannula 26, can also be used to connect to both channels 27 and 37 and simultaneously inflate upper flange 20 and lower flange 30 with the means to assure upper flange 20 is inflated to a greater extent or size, said means exemplified by a check valve or an orifice of a larger diameter.

In certain embodiments compression devices 10 or 11 are made of non-resorbable polymers and metals or composites, preferably from polymeric and elastomeric materials. In one embodiment, inflatable flanges are non-compliant balloons whereby they are made of materials with low elasticity, low elastomeric properties materials, such as PET, whereby upon reaching the expanded state, increase of inflating pressure does not result in appreciable increase in size of the balloon. They are excreted as the stapled areas of tissues T1 and T2 eventually undergo necrotic transformation and die off.

In certain embodiments compression devices 10 and 11 are made of resorbable or erodible/soluble materials which are known to a skilled artisan. In certain embodiments only upper flange 20 and 21 and lower flange 30 are erodible/soluble, with time to at least partially dissolve from about 3 days to about 30 days in the gastro-intestinal (GI) tract, such as 1 week, 2 weeks, 3 weeks, or 4 weeks, most preferably 2-4 weeks. Partial dissolution is defined as dissolution sufficient enough to result in deflation.

In certain embodiments inflatable flanges 20 and 30 are not per se rapidly soluble or erodible in the GI tract, however inflatable flanges 20 and 30 have at least one deflation plug which is soluble or erodible in the GI environment and such plug defines the rate of deflating of flanges 20 and 30. Upon dissolution of the plug, flanges 20 and 30 deflate releasing compression devices 10 or 11 resulting in devices 10 or 11 excretion. For the deflation plug the time to at least partially dissolve is from about 3 days to about 30 days in the gastro-intestinal (GI) tract, such as 1 week, 2 weeks, 3 weeks, or 4 weeks, most preferably 2-4 weeks. Partial dissolution is defined as dissolution sufficient enough to result in deflation.

Figure 15:
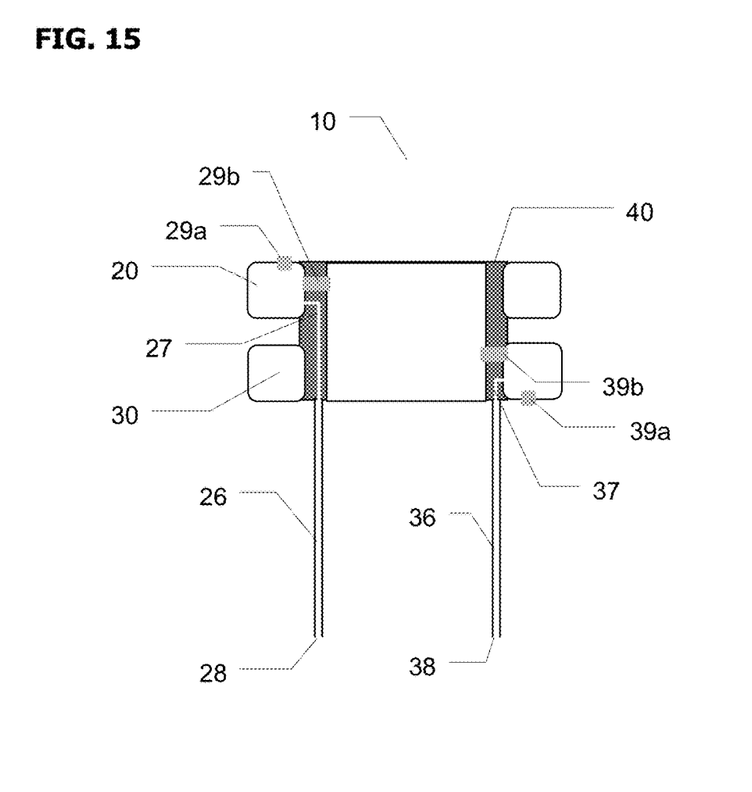

FIG. 15 shows embodiments of device 10 having soluble/erodible deflation plugs 29a and 29b installed to deflate upper flange 20 and soluble/erodible deflation plugs 39a and 39b installed to deflate lower flange 30.

According to one embodiment of the present invention, the sequence of using the inflatable compression device of the present invention for establishing an anastomotic joint is as follows:
a) Axially positioning the inflatable compression device on the anvil
b) Axially inserting the anvil into the tubular tissue T1
c) Axially inserting the anastomotic stapler into tubular tissue T2
d) Connecting the anvil to the stapling head via the anvil shaft
e) Approximating the anvil and the stapling head and compressing tubular tissues T1 and T2 between the stapling head and the anvil
f) Firing the anastomotic stapler and establishing stapled anastomotic joint between tissues T1 and T2
g) Partially withdrawing the anastomotic stapler thus positioning the inflatable compression device with the upper flange above the stapled areas of tissues T1 and T2 and the lower flange below the stapled areas of tissues T1 and T2
h) Expanding the upper flange e.g. by inflating it prior to step f), immediately after step f), or immediately after step g), if the inflatable compression device has inflatable upper flange
i) Expanding the lower flange, e.g. by inflating it, thus compressing the stapled areas of tissues T1 and T2 between the upper flange and the lower flange
j) Removing the anastomotic stapler from the tubular tissue T2, separating the anastomotic stapler from the inflatable compression device and leaving the inflatable compression device within tubular tissues T1 and T2 with the upper flange above the stapled areas of tissues T1 and T2 and the lower flange below the stapled areas of tissues T1 and T2

Additional steps after the inflatable compression device installation include:
   Optionally releasing antimicrobial agents from the inflatable compression device
   Deflating the inflatable compression device and allowing the inflatable compression device to pass through the GI tract out of the body Complete steps of anastomotic surgical procedures, e.g. application of purse string sutures are not listed above, but will be known to skilled artisans.

Figure 16:
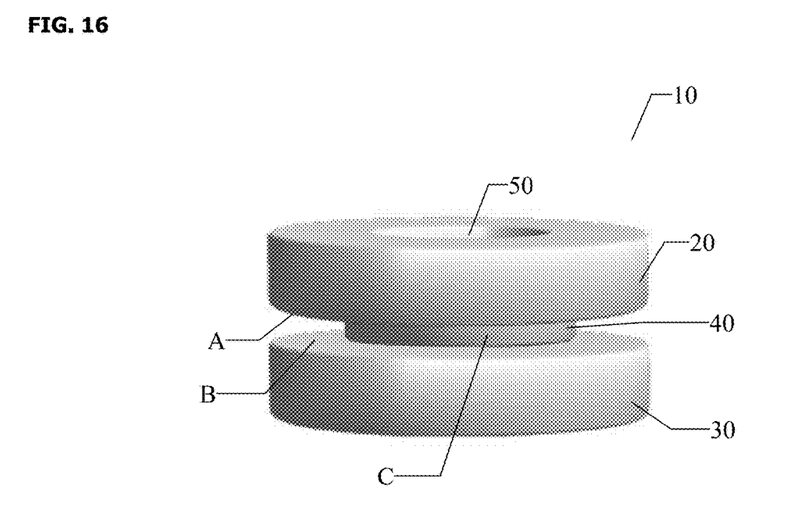
FIGS. 16 and 17 show a perspective view of an embodiment of the compression device of the present invention
Figure 17:
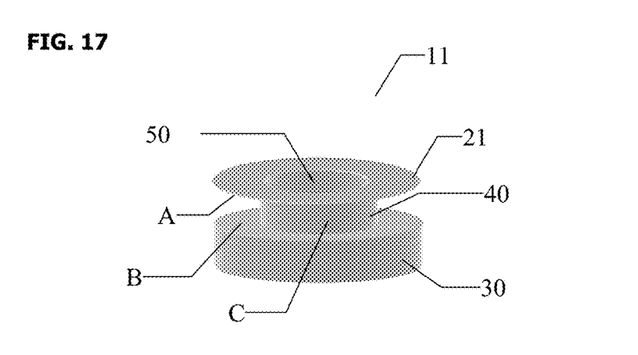

According to the present invention, compression devices 10 or 11 are optionally at least partially coated or impregnated with releasable antimicrobial agents. All portions of devices 10 and 11 can be treated with such agents, or specific outside portions of devices 10 and 11 which are in contact with areas of tissues T1 and T2 which are stapled or cut, are preferably coated or impregnated with releasable antimicrobial agents. Referring to FIGS. 16, 17, one or more of the following areas are preferably coated or impregnated with releasable antimicrobial agents: Area A on the lower side of upper flange 20 or 21; area B on the upper side of lower flange 30; area C on the external surface of tubular body 40 between upper flange 20 or 21 and lower flange 30.

Advantageously, compression devices 10 or 11 isolate areas of stapled and cut tissue from the GI environment and establish a concentration of anti-microbial agents in the immediate vicinity of these areas of tissue. Such treatment is thought to minimize formation of tissue ulcerations and other defects and decrease the occurrence of anastomotic leaks.

The diameter of disk-shaped upper flange 21 and inflated upper flange 20 and inflated lower flange 30 is conforming generally to the diameter of stapling head 600 and anvil 1000 and to the geometry/inner diameter of tubular tissue T1 and T2. In some embodiments, diameter of upper flange 21 and inflated upper flange 20 and inflated lower flange 30 is from about 15 mm to about 30 mm, such as 20 mm, 22 mm, 25 mm. The diameter of non-inflated upper flange 20 and lower flange 30 is at least 25% smaller vs. the inflated diameter, such as 25%, 30% or 50% smaller.

The diameter of the opening forming an axial passage through upper flange 20, lower flange 30, and tubular body 40 is from about 10 mm to about 20 mm. The wall thickness of the tubular body 40 is from about 0.5 mm to about 5 mm, such as 1, 2, 3 mm.

The height of the disk-shaped upper flange 21 is about 0.5 mm to about 5 mm, such as 1, 2, or 3 mm. The height of inflated upper flange 20 and inflated lower flange 30 is from about 2 mm to about 10 mm, more preferably 3 to 8 mm, such as 3, 4, or 6 mm, Gap G between upper flange 20 or 21 and lower flange 30 in inflated position is from 0 mm (i.e. upon inflation in absence of tissue T1 and T2 present in the gap G, upper flange 20 or 21 touches lower flange 30) to about 0.5 to 2 mm, such as 0.5 mm or 1 mm. When device 10 is installed on stapled tissue, Gap G corresponds to thickness of compressed tissues T1 and T2 between upper flange 20 or 21 and lower flange 30.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A circular stapling instrument comprising:
   a) An anvil
   b) A stapling head assembly
   c) A moveable shaft connecting the anvil and staple head assembly;
   d) A longitudinal shaft from which the moveable shaft extends;
   e) A compression device removeably affixed to the anvil and having an upper ring-shaped or disk-shaped flange at a distal end of said device connected to a lower ring-shaped expandable flange at a proximal end of said device via a hollow cylindrical tubular body and an opening forming an axial passage through said upper flange, lower flange, and tubular body,
   wherein said lower flange is inflatable via an inflation cannula in fluid communication with said lower expandable flange.

2. The compression device of claim 1, wherein said device is generally barbell-shaped.

3. The compression device of claim 1, wherein said upper flange is ring-shaped and expandable.

4. The compression device of claim 3, wherein said upper flange is inflatable.

5. The compression device of claim 1, wherein at least a portion of said compression device is erodible in a mammalian gastrointestinal tract over a period ranging from 1 to 4 weeks.

6. The compression device of claim 1, wherein said compression device is at least partially coated or impregnated with a releasable anti-bacterial, anti-microbial, anti-infective agent, or combinations thereof.

7. The compression device of claim 6, wherein at least 50% of said agent is released over the first 1 to 2 weeks after implantation of said compression device in a joined tubular tissue section.

8. The compression device of claim 1, wherein said compression device is affixed to said anvil at said lower flange.

9. A circular anastomosis stapler kit comprising:
   a) A compression device having an upper ring-shaped or disk-shaped flange at a distal end of said device connected to a lower ring-shaped expandable flange at a proximal end of said device via a hollow cylindrical tubular body and an opening forming an axial passage through said upper flange, lower flange, and tubular body; and
   b) An anastomotic stapler comprising a stapling head and an anvil moveable longitudinally relative to the stapling head and mounted on an axially extending moveable shaft, wherein said compression device can be releasably attachable to said anvil, and wherein said lower flange is inflatable via an inflation cannula in fluid communication with said lower expandable flange.

* * * * *